US008295948B2

(12) United States Patent
Barker et al.

(10) Patent No.: US 8,295,948 B2
(45) Date of Patent: Oct. 23, 2012

(54) TUBULAR LEAD ANCHOR AND METHODS AND DEVICES USING THE ANCHOR

(75) Inventors: John Michael Barker, Ventura, CA (US); Kristen N. Jaax, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 233 days.

(21) Appl. No.: 12/506,892

(22) Filed: Jul. 21, 2009

(65) Prior Publication Data

US 2011/0022142 A1 Jan. 27, 2011

(51) Int. Cl.
*A61N 1/04* (2006.01)

(52) U.S. Cl. ......... 607/132; 607/117; 607/126; 600/386

(58) Field of Classification Search .............. 607/116, 607/117, 130, 132; 600/386, 390
See application file for complete search history.

(56) References Cited

U.S. PATENT DOCUMENTS

| 51,582 | A | * | 12/1865 | Gibbs | 24/129 R |
|---|---|---|---|---|---|
| 59,277 | A | * | 10/1866 | Sawyer | 24/129 R |
| 2,475,339 | A | * | 7/1949 | Sandy | 24/129 R |
| 2,903,772 | A | * | 9/1959 | McKinlay | 24/129 R |
| 3,888,448 | A | * | 6/1975 | Rowland | 248/328 |
| 4,266,552 | A | | 5/1981 | Dutcher et al. | |
| 4,276,882 | A | | 7/1981 | Dickhudt et al. | |
| 4,374,527 | A | * | 2/1983 | Iversen | 607/117 |
| 4,419,819 | A | | 12/1983 | Dickhudt et al. | |
| 5,036,862 | A | | 8/1991 | Pohndorf | |
| 5,273,053 | A | | 12/1993 | Pohndorf | |
| 5,476,493 | A | | 12/1995 | Muff | |
| 5,628,780 | A | * | 5/1997 | Helland et al. | 607/126 |
| 5,746,722 | A | | 5/1998 | Pohndorf et al. | |
| 5,843,146 | A | | 12/1998 | Cross, Jr. | |
| 6,181,969 | B1 | | 1/2001 | Gord | |
| 6,210,417 | B1 | | 4/2001 | Baudino et al. | |
| 6,473,654 | B1 | | 10/2002 | Chinn | |
| 6,516,227 | B1 | | 2/2003 | Meadows et al. | |
| 6,554,802 | B1 | | 4/2003 | Pearson et al. | |
| 6,609,029 | B1 | | 8/2003 | Mann et al. | |
| 6,609,032 | B1 | | 8/2003 | Woods et al. | |
| 6,741,892 | B1 | | 5/2004 | Meadows et al. | |
| 6,901,287 | B2 | | 5/2005 | Davis et al. | |
| 6,985,777 | B2 | | 1/2006 | Tsuboi et al. | |
| 7,082,337 | B2 | | 7/2006 | Sommer et al. | |
| 7,099,718 | B1 | | 8/2006 | Thacker et al. | |

(Continued)

FOREIGN PATENT DOCUMENTS

EP 597213 B1 5/1994

(Continued)

OTHER PUBLICATIONS

U.S. Appl. No. 11/238,240, filed Sep. 29, 2005.

*Primary Examiner* — Carl H Layno
*Assistant Examiner* — Eugene Wu
(74) *Attorney, Agent, or Firm* — Frommer Lawrence & Haug LLP; Bruce E. Black

(57) ABSTRACT

A lead anchor includes a plurality of parallel tubular members and at least one suture element configured and arranged for receiving a suture to suture the lead anchor to patient tissue. Each tubular member defines a lead lumen having a first opening and a second opening through which a lead can pass.

20 Claims, 11 Drawing Sheets

U.S. PATENT DOCUMENTS

| | | |
|---|---|---|
| 7,107,105 B2 | 9/2006 | Bjorklund et al. |
| 7,184,841 B1 | 2/2007 | Bodner et al. |
| 7,244,150 B1 | 7/2007 | Brase et al. |
| 2003/0114905 A1 | 6/2003 | Kuzma |
| 2004/0034972 A1* | 2/2004 | Brown .................. 24/129 R |
| 2004/0059392 A1 | 3/2004 | Parramon et al. |
| 2005/0165465 A1 | 7/2005 | Pianca et al. |
| 2005/0183245 A1* | 8/2005 | Whipple .................. 24/129 R |
| 2007/0050005 A1 | 3/2007 | Lauro |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0219595 A1 | 9/2007 | He |
| 2007/0239243 A1 | 10/2007 | Moffitt et al. |
| 2008/0071320 A1 | 3/2008 | Brase |
| 2008/0196939 A1 | 8/2008 | Lubenow et al. |
| 2008/0243220 A1 | 10/2008 | Barker |
| 2009/0254151 A1 | 10/2009 | Anderson et al. |

FOREIGN PATENT DOCUMENTS

| | | |
|---|---|---|
| EP | 625359 A2 | 11/1994 |
| EP | 988080B1 A1 | 2/2007 |
| WO | 9848880 A1 | 11/1998 |
| WO | 2008101026 A1 | 8/2008 |
| WO | 2008121708 A2 | 10/2008 |

* cited by examiner

TUBULAR LEAD ANCHOR AND METHODS AND DEVICES USING THE ANCHOR

FIELD

The invention is directed to lead anchors for implantable devices, as well as the implantable devices themselves, and methods of manufacture and use of the lead anchors and implantable devices. The invention is also directed to tubular lead anchors for implantable spinal cord stimulators, as well as the implantable spinal cord stimulators, and methods of manufacture and use of the lead anchors and the implantable spinal cord stimulators.

BACKGROUND

Spinal cord stimulation is a well accepted clinical method for reducing pain in certain populations of patients. Implantable stimulation devices have been developed to provide therapy for a variety of treatments. For example, implantable stimulation devices can be used to stimulate nerves, such as the spinal cord, muscles, or other tissue. An implantable stimulation device typically includes an implanted control module (with a pulse generator), a lead, and an array of stimulator electrodes. The stimulator electrodes are implanted in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

The stimulator electrodes are coupled to the control module by the lead and the control module is implanted elsewhere in the body, for example, in a subcutaneous pocket. The lead is often anchored at one or more places in the body to prevent or reduce movement of the lead or stimulator electrodes within the body which could damage tissue, move the stimulator electrodes out of the desired position, or interrupt the connection between the stimulator electrodes and the control module.

Many conventional lead anchors possess inadequate lead retention strength when the lead is subjected to tensile loading. This may cause the lead to migrate proximally from the desired neurostimulation site. According to recent studies, lead migration occurs in approximately 13% of cases. Additional studies suggest that electrode migration may be the most common reason for failure to maintain long-term pain control with spinal cord stimulation. Other problems associated with lead migration include lead breakage, and loose connection.

Yet another problem associated with conventional lead anchors is that they typically contain moving, multi-part mechanisms or locks that could unintentionally disengage after implantation. The added complexity may cause lead migration and breakage as explained above.

BRIEF SUMMARY

One embodiment is a lead anchor having a plurality of parallel tubular members and at least one suture element configured and arranged for receiving a suture to suture the lead anchor to patient tissue. Each tubular member defines a lead lumen having a first opening and a second opening through which a lead can pass.

Another embodiment is a method of implanting an implantable stimulation device. The method includes implanting a portion of a lead having an electrode array near tissue to be stimulated. A distal end of the lead is secured through a lead anchor. The lead anchor includes a plurality of parallel tubular members, each tubular member defining a lead lumen having a first opening and a second opening through which a lead can pass, and at least one suture element configured and arranged for receiving a suture. The lead anchor is secured to the surrounding tissue using sutures.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of lead anchors used with elongate implantable devices such as spinal cord leads, cardiac pacing leads or catheters, implantable devices or systems containing the lead anchors, methods of use and manufacture of lead anchors and implantable devices. In addition, the invention is directed to lead anchors for implantable spinal cord stimulators, as well as the stimulators themselves and methods of use and manufacture of the lead anchors and spinal cord stimulators.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
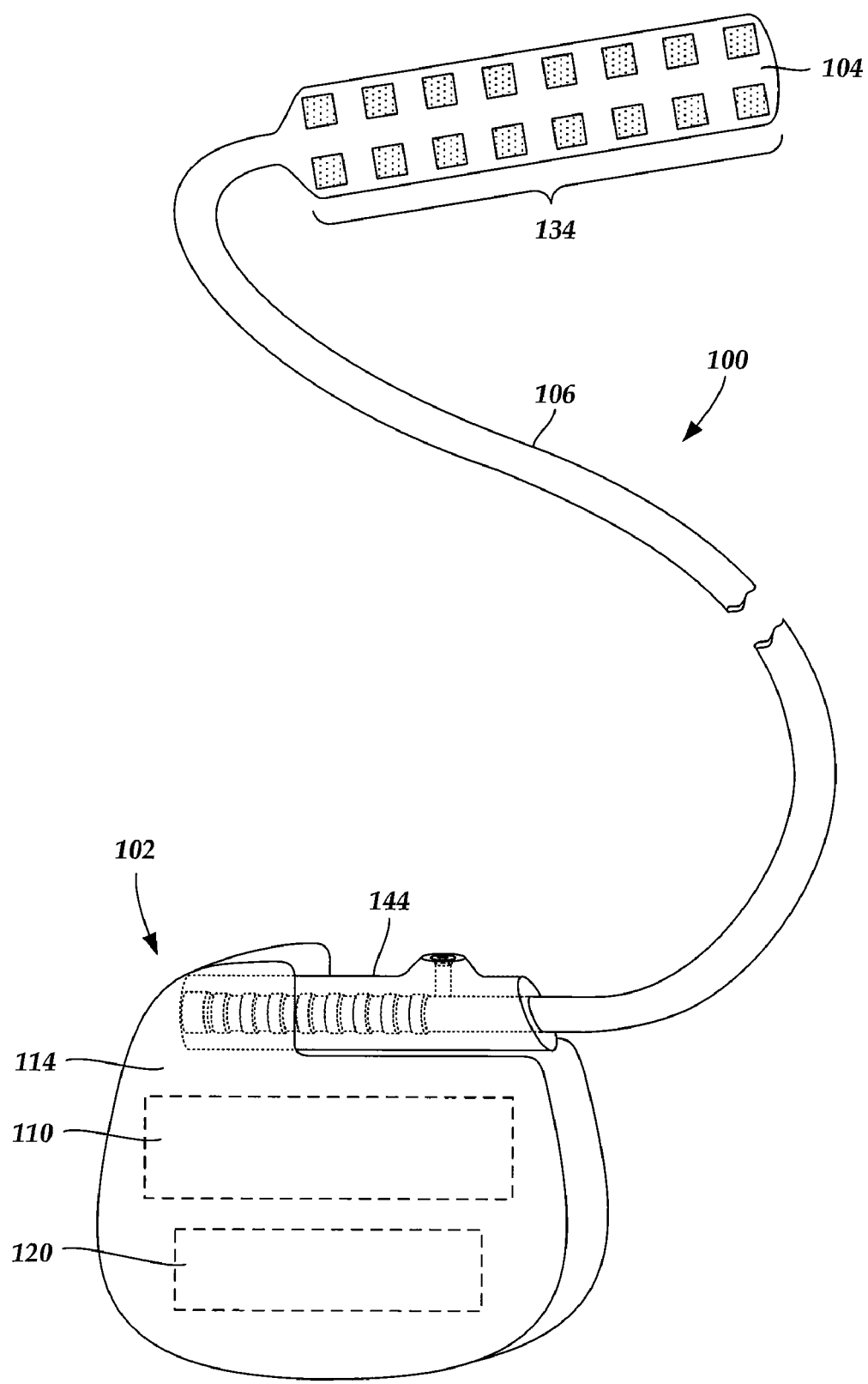
FIG. 1 is a schematic perspective view of one embodiment of an electrical stimulation system, according to the invention.
Figure 2:
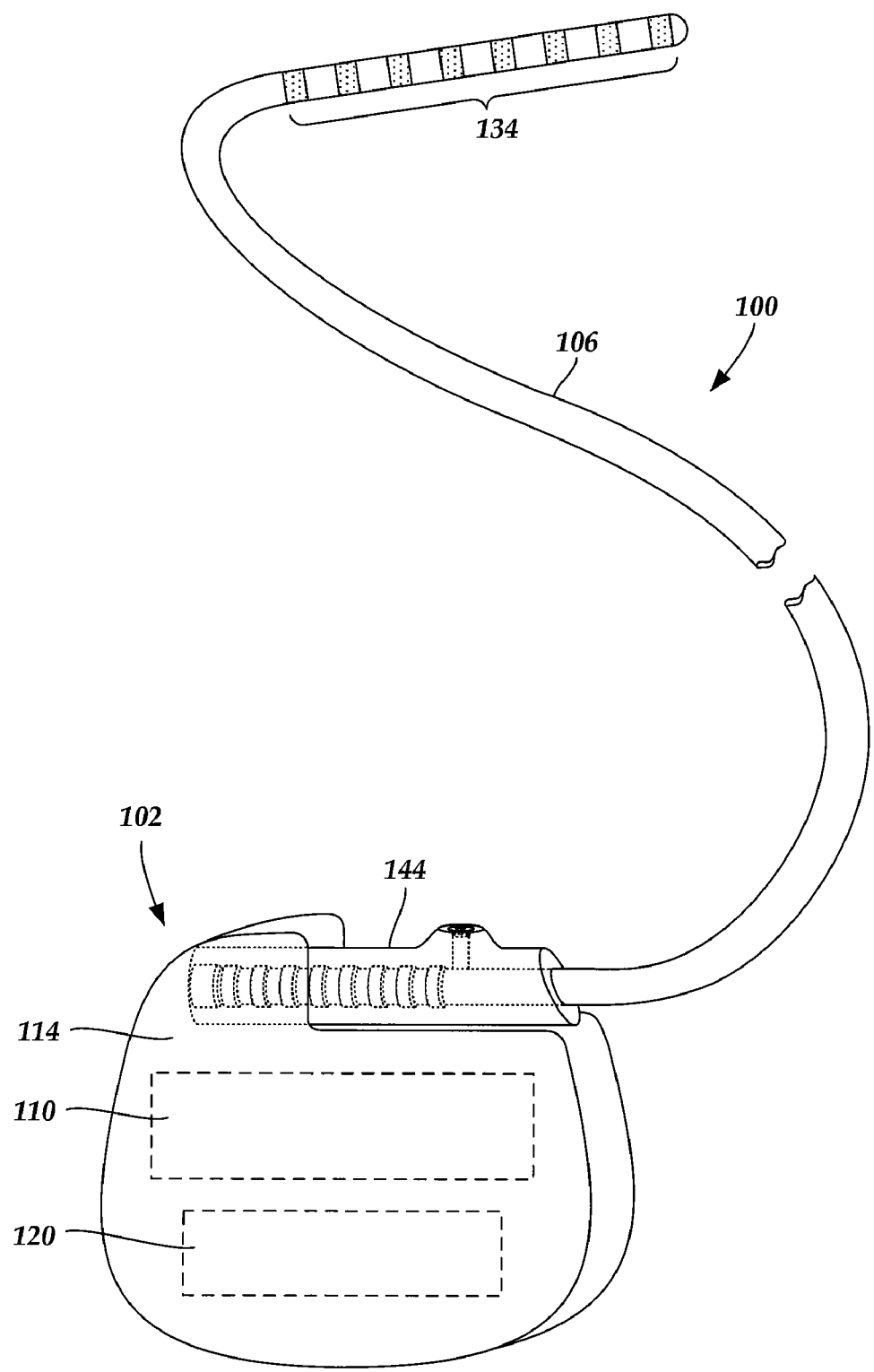
FIG. 2 is a schematic perspective view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via connector contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone, epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding connector contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as connector contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductors may be embedded in the non-conductive material of the lead or can be disposed in one or more lumens (not shown) extending along the lead. In some embodiments, there is an individual lumen for each conductor. In other embodiments, two or more conductors may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
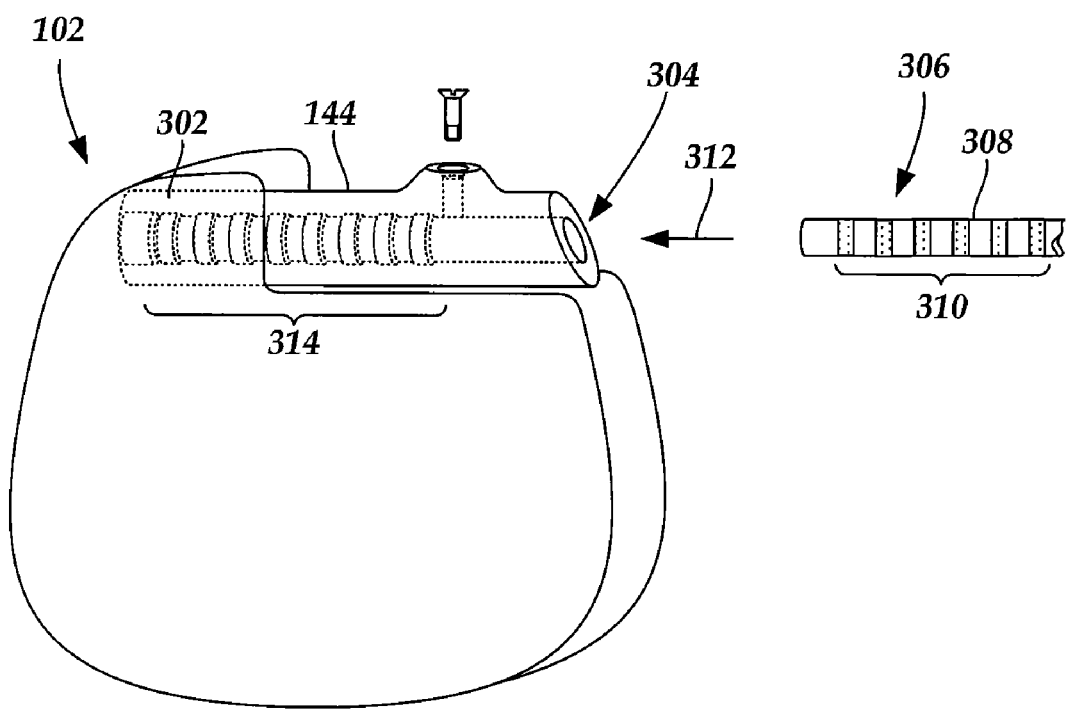
FIG. 3A is a schematic perspective view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of connector contacts 314 for each port 304. When the lead 308 is inserted into the port 304, the connector contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
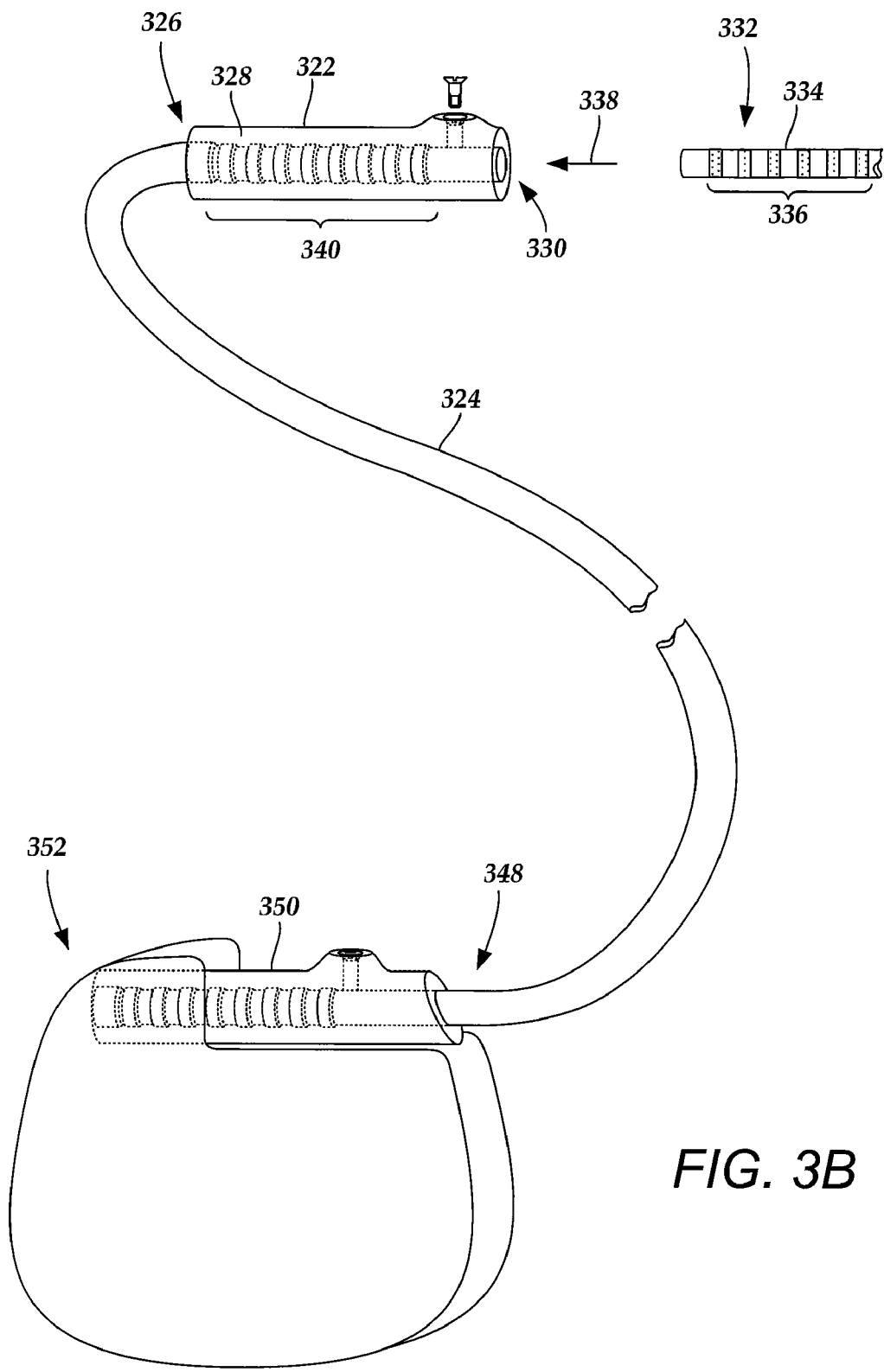
FIG. 3B is a schematic perspective view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of connector contacts 340. When the lead 334 is inserted into the port 330, the connector contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductors (not shown) that electrically couple the connector contacts 340 to a proximal end 348 of the lead extension 324 that is opposite to the distal end 326. In at least some embodiments, the conductors disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

A lead anchor can be used in an implantable device, such as an implantable spinal cord stimulator, to anchor a lead connecting a control module to an electrode array. The lead anchor includes a plurality of tubular members for receiving the lead. In at least some embodiments, the lead anchor also contains a flange coupled to the tubular members.

Figure 4A:
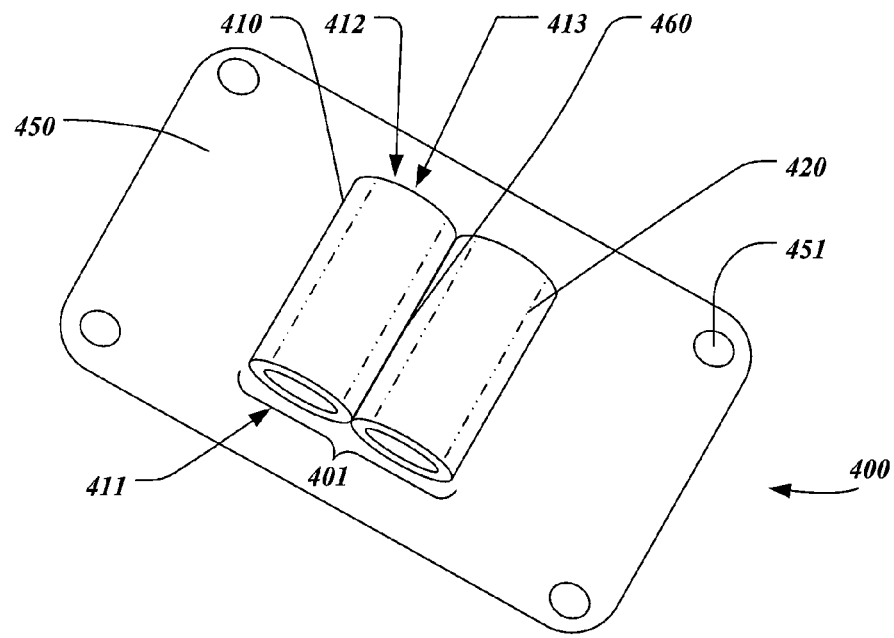
FIG. 4A is a schematic perspective view of one embodiment of a tubular lead anchor, according to the invention.

FIG. 4A is a schematic view of one embodiment of a tubular lead anchor. As shown in FIG. 4A, the tubular lead anchor 400 includes a plurality of tubular members 401 for receiving a lead. The plurality of tubular members 401 may be made of a metal such as titanium, nickel, aluminum, stainless steel, copper, gold, silver, platinum and alloys thereof or any other biocompatible metal suitable for implantation. Alternatively, the plurality of tubular members 401 may be made of a polymer or plastic, for example, silicone, polyvinyl chloride, fluoropolymers, polyurethane, polycarbonate, acrylic compounds, thermoplastic polyesters, polypropylene, low-density polyethylenes, other thermoplastic polymers or any combination thereof. The tubular member may be rigid or flexible.

In FIG. 4A, the lead anchor 400 is formed of a first tubular member 410 and a second tubular member 420. Each tubular member has a first opening and a second opening, which define a lead lumen. In some embodiments, a tubular member is formed in the shape of a cylinder so that all cross-sections down the length of the tubular member are substantially circular and have the same radius. In other embodiments, the tubular member has a greater radius near the first opening than the radius at the second opening. Thus, in some embodiments the tubular member may be in the shape of a cone. In other embodiments, the tubular member has a cross-section that is rectangular, triangular, ovoid, or any other suitable shape that is large enough to house a lead. Furthermore, in some embodiments the lead lumen may be defined so that the lead passes directly through the center of the tubular member. In other embodiments, the lead lumen is defined as a curved or tortuous path through the tubular member. The first opening and second opening of each tubular member may be a friction fit or can be large enough to allow the lead to pass through freely. It will be understood that all combinations discussed above may be applied to either the first tubular member 410, the second tubular member 420 or both. In some embodiments containing more than two tubular members, each tubular member may be formed through any of the methods or a combinations of the methods discussed herein. Furthermore, it is contemplated that in at least some embodiments, the two tubular members are different in shape, composition, makeup or size.

The tubular lead anchor 400 of FIG. 4A further contains an optional flange 450 attached to the plurality of tubular members 401. The flange 450 may be formed of a metal such as titanium, nickel, aluminum, stainless steel, copper, gold, silver, platinum and alloys thereof or any other biocompatible metal suitable for implantation. Alternatively, the flange may be made of a polymer or plastic, such as silicone, polyvinyl chloride, fluoropolymers, polyurethane, polycarbonate, acrylic compounds, thermoplastic polyesters, polypropylene, low-density polyethylenes and other thermoplastic elastomers, or any combination thereof. The flange 450 may be made of the same material as the plurality of tubular members 401 or a different material. Furthermore, the flange 450 may be made in any shape such as rectangular, circular, ovoid, triangular or any other suitable shape. The flange 450 may be coupled to the plurality of tubular members 401 by any manner known in the art, including but not limited to setting, fixing, screwing, adhering, welding, attaching, fastening, gluing, or any other method suitable for coupling the flange to the plurality of tubular members. In at least some embodiments, the flange 450 and the plurality of tubular members 401 are unitary (e.g. formed together by, for example, molding or any other suitable method).

The flange 450 may further define suture elements 451. The suture elements 451 may be grooves, stubs, ridges, eyelets, openings or bores or any other suitable arrangement for suturing the tubular lead anchor 400 to the fascia, ligament or other tissue. Though FIG. 4A discloses four suture elements, any number of suture elements may be used. Furthermore, the suture elements 451 may also be in any combination of the arrangements described above, e.g. a combination of grooves, stubs, ridges, eyelets, opening, bores, or any other suitable arrangement. In FIG. 4A, the suture elements 451 are positioned in the corners of the flange 450, however it is contemplated that they may be disposed anywhere on the flange 450. In some embodiments, a recess 460 between the plurality of tubular members 401 can be used for suturing. The recess 460 may be a concavity, space, notch, or depression between any two tubular members. In at least some embodiments, the tubular lead anchor 400 will have both the suture elements 451 and a recess 460. In some embodiments, the flange 450 or plurality of tubular members 401 can be stapled to the tissue instead of, or in addition to, suturing.

Figure 4B:
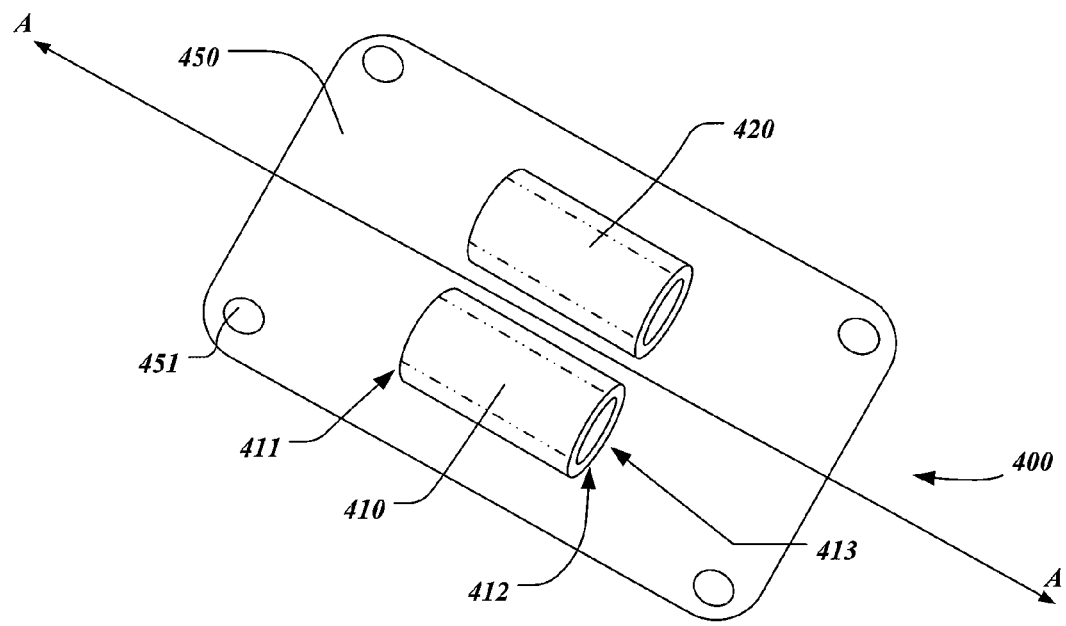
FIG. 4B is a schematic perspective view of another embodiment of a tubular lead anchor, according to the invention.

FIG. 4B is a schematic view of another embodiment of a tubular lead anchor 400. In some embodiments, as seen above, the plurality of tubular members 401 are disposed adjoining one another. Conversely, the plurality of tubular members 401 may also be spaced apart as seen in FIG. 4B. The distance between the first tubular member 410 and the second tubular member 420 may be defined at any desired interval. Furthermore, the first tubular member 410 may be positioned in any arrangement with respect to the second tubular member 420. In some embodiments, the first tubular member 410 and the second tubular member 420 are parallel or substantially parallel. The placement of the plurality of tubular members 401 may also vary with respect to the flange 450. For example, the plurality of tubular members 401 may be substantially parallel to or perpendicular to the central axis A of the flange 450.

Figure 5:
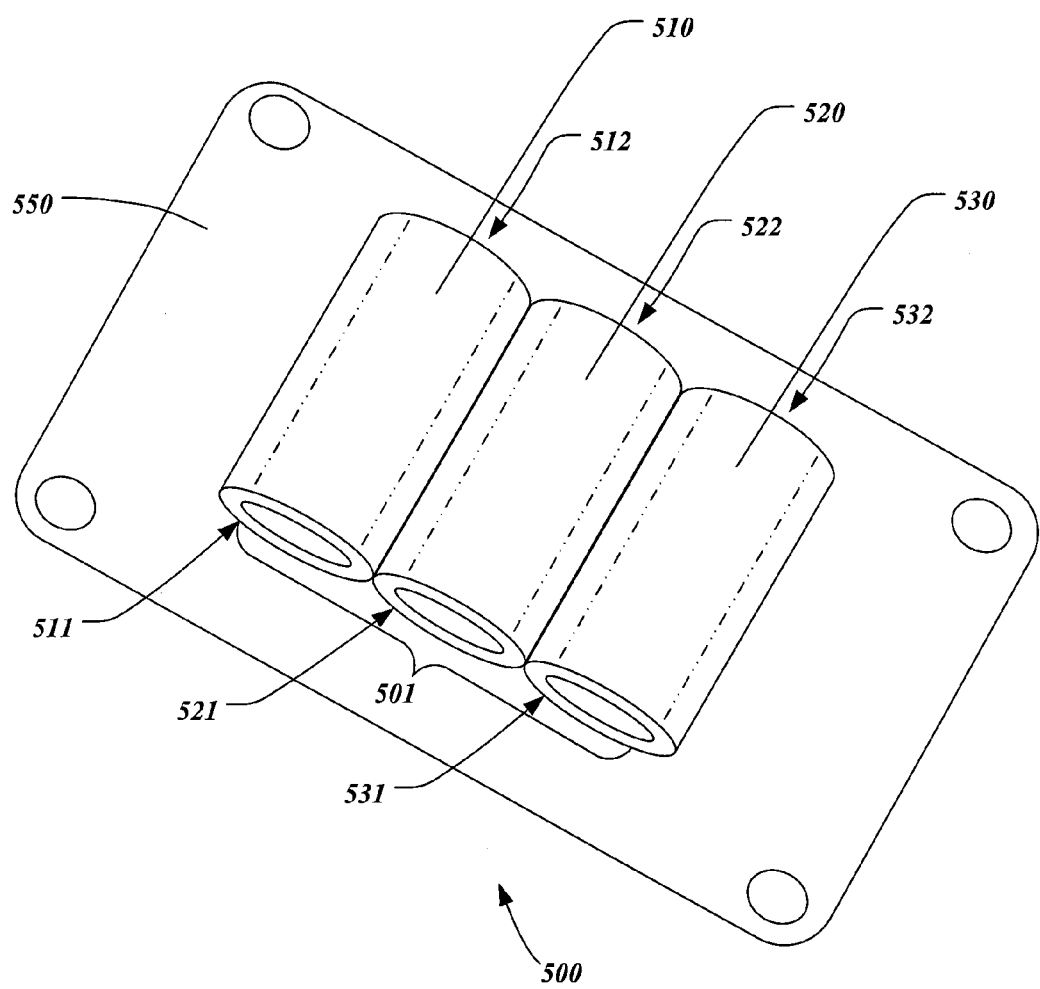
FIG. 5 is a schematic perspective view of a third embodiment of a tubular lead anchor, with three tubular members, according to the invention.
Figure 8:
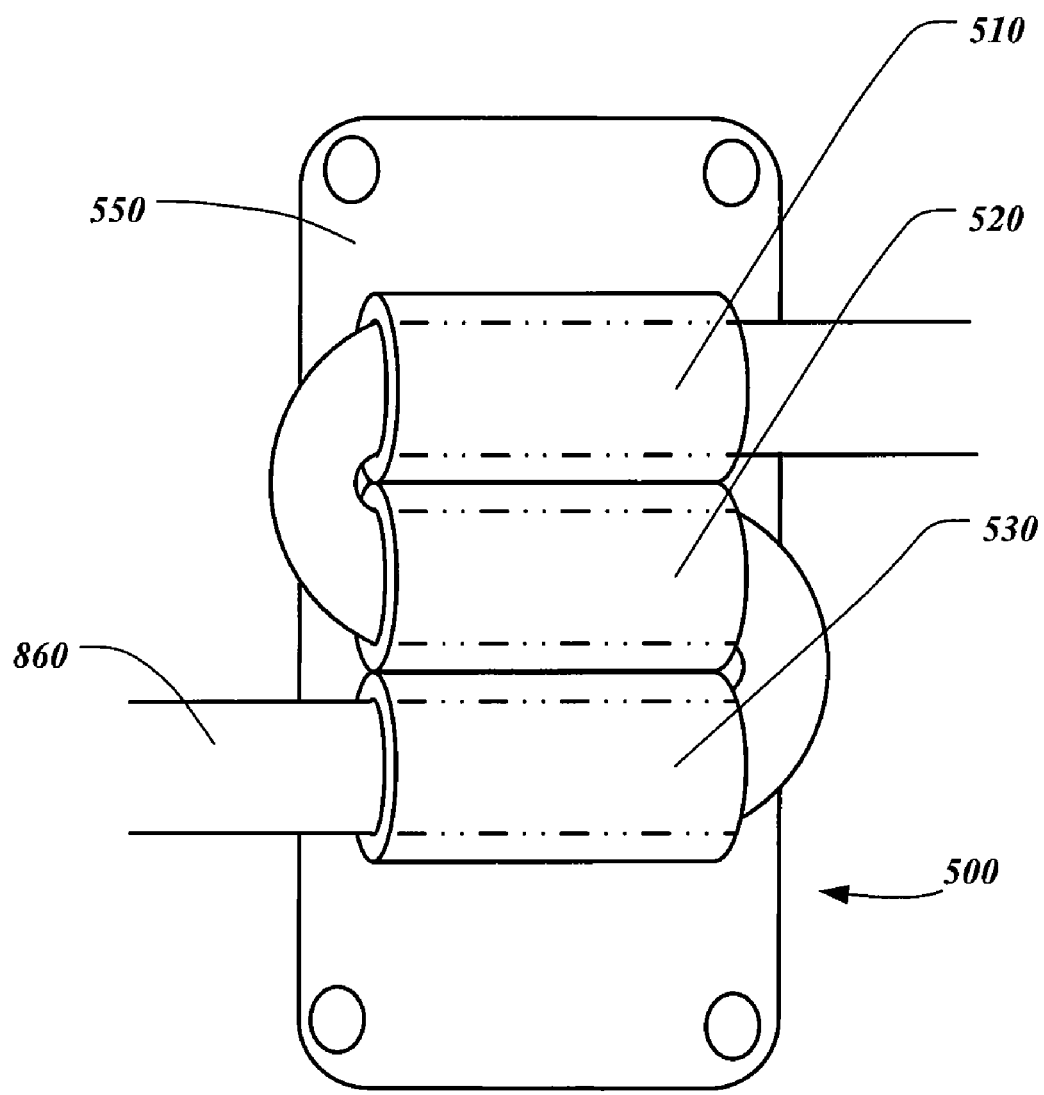
FIG. 8 is a schematic perspective view of the tubular lead anchor of FIG. 5 after a lead has been inserted in the lead anchor, according to the invention.

FIG. 5 is a schematic view of another embodiment of a tubular lead anchor 500 with a plurality of tubular members 501. In some embodiments, the plurality of tubular members 501 may have any number of tubular members. In some other embodiments, the tubular lead anchor 500 has a first tubular member 510, a second tubular member 520 and a third tubular member 530. The third tubular member 530 may be formed in any shape and located in any position as described above in reference to the first tubular member 510. When a third tubular member 530 is introduced several options for lead retention are available. For example, the lead may be passed through any one, two or all three of the tubular members. In some embodiments, the lead is passed from the first opening 511 to the second opening 512 of the first tubular member 510, then from the second opening 522 to the first opening 521 of the second tubular member 520, and finally from the first opening 531 to the second opening 532 of the third tubular member 530 as shown in FIG. 8. In at least some other embodiments, the lead is passed only from the first opening 511 to the second opening 512 of the first tubular member 510 and from the second opening 532 to the first opening 531 of the third tubular member 530, completely bypassing the second tubular member. It will be understood that the lead may be passed through any combination and in any sequence of openings of the various tubular members. Furthermore, as will be described in more detail, the lead may also passed in a non-planar manner.

Furthermore, it may be useful for any or all parts of the lead anchor to be made of a material that is radiopaque, so that it is visible under fluoroscopy or other forms of x-ray diagnosis. In some embodiments, the flange is radiopaque. In some embodiments, at least one of the tubular members is radiopaque so as to allow the lead anchor to be readily identified under fluoroscopy or other forms of x-ray diagnosis. The lead itself may also be radiopaque.

Figure 6A:
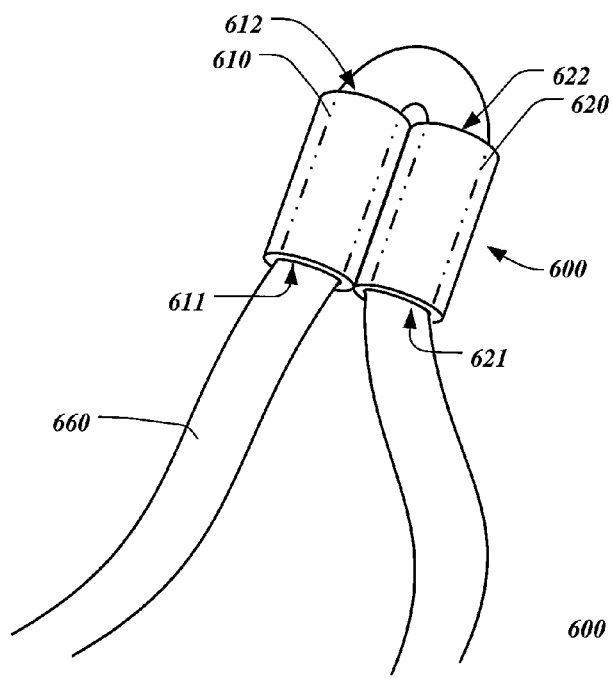
FIG. 6A is a schematic perspective view of a fourth embodiment of a tubular lead anchor, after a lead has been inserted into the lead anchor, according to the invention.
Figure 6B:
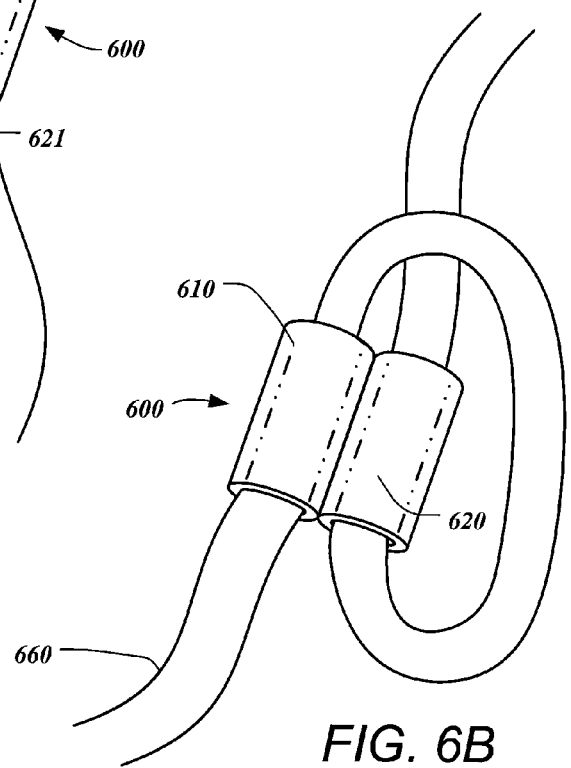
FIG. 6B is a schematic perspective view of another embodiment of a tubular lead anchor, after a lead has been inserted into the lead anchor using the looping method, according to the invention.
Figure 6C:
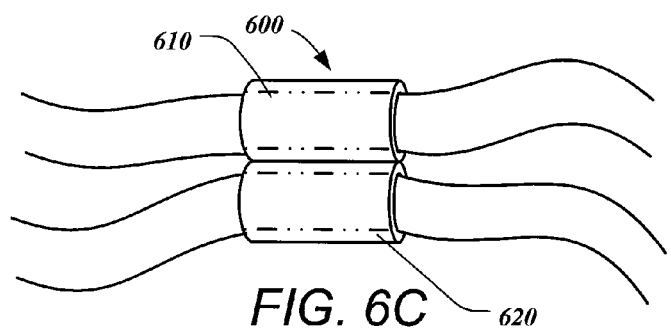
FIG. 6C is a schematic perspective view of another embodiment of a tubular lead anchor, after multiple leads have been inserted into the lead anchor, according to the invention.

FIGS. 6A-C are schematic views of several embodiments of a tubular lead anchor 600 after a lead 660 has been inserted into the lead anchor. The tubular lead anchor 600 is formed of a first tubular member 610 and a second tubular member 620. In some embodiments, shown in FIG. 6A, the lead 660 is inserted from the first opening 611 to the second opening 612 of the first tubular member 610 and then from the second opening 622 to the first opening 621 of the second tubular member 620. Between the second opening 612 of the first tubular member 610 and the second opening 622 of the second tubular member 620, the lead 660 may be passed to form a sharp 1800 curve, referred to as a single hairpin. In some embodiments, the lead 660 is tightly passed through the first and second tubular members so that there is no excess or slack in between the two members. This natural tight kink of the radiopaque lead produces excellent visualization of the anchor site under fluoroscopy. In at least some other embodiments, a portion of the lead 660 is intentionally left as slack between the first and second tubular members for strain relief in the lead 660. While FIG. 6A shows a lead 660 making a hairpin turn between the first tubular member 610 and the second tubular member 620, other methods are available for coupling the lead to the lead anchor. As shown in FIG. 6B, in some embodiments, the lead 660 is fed through the first tubular member 610, looped and then inserted into the second tubular member 620. This single loop arrangement provides an alternative method for securing the lead. The single loop arrangement may be formed by disposing the lead through the first opening of the first tubular member, the lead lumen of the first tubular member, and the second opening of the first tubular member, then disposing it through the first opening of the second tubular member, the lead lumen of the second tubular member, and the second opening of the second tubular member. FIG. 6C shows one embodiment where multiple leads are utilized. In at least some other embodiments, a first lead may be introduced through the first tubular member 610, while a second lead may be introduced through the adjacent second tubular member 620. These embodiments group multiple leads and aid in anchoring them at one point on the patient fascia. In embodiments grouping multiple leads the lead anchor is also useful in providing one separate device for anchoring as opposed to multiple devices and overall reduces the bulk and the number of implanted parts.

Figure 7:
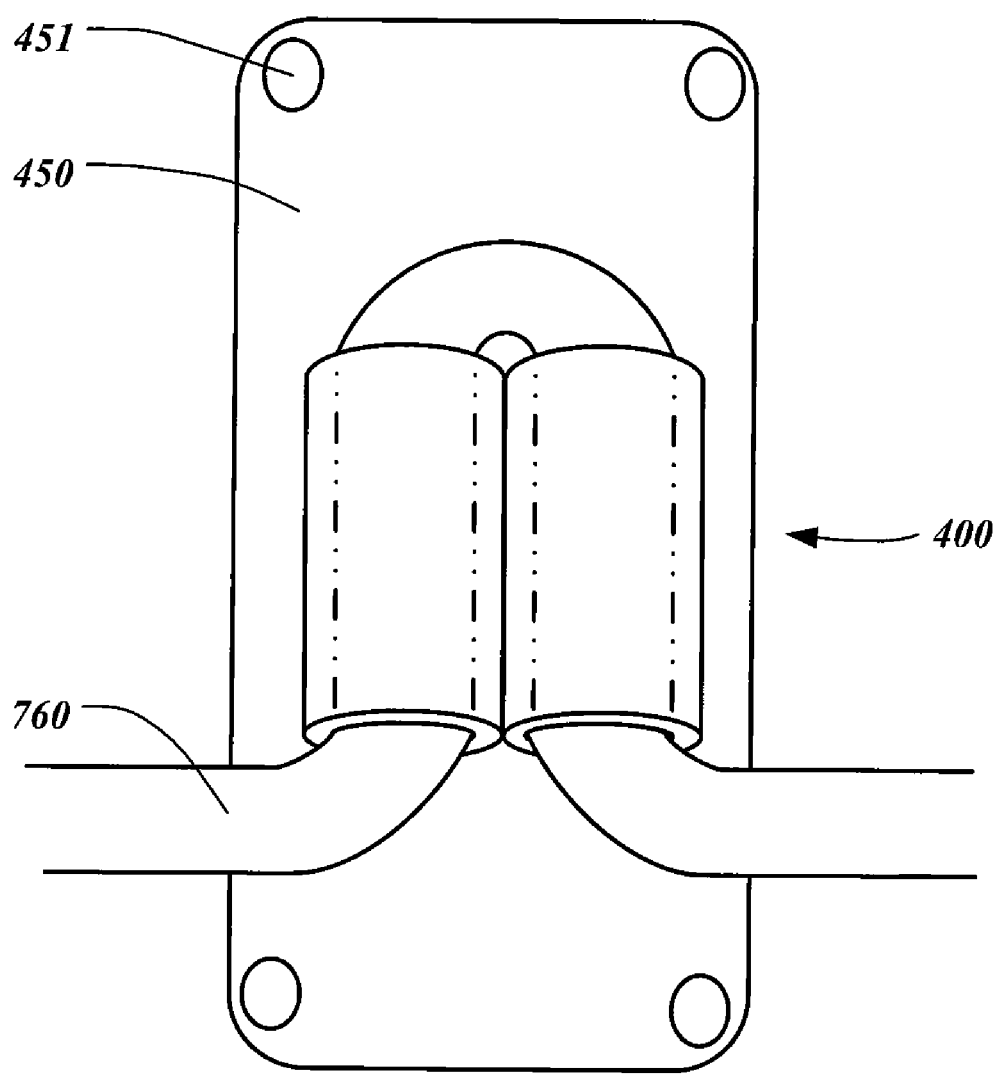
FIG. 7 is a schematic perspective view of the tubular lead of FIG. 4B after a lead has been inserted in the lead anchor, according to the invention.

FIG. 7 is a schematic view of the tubular lead anchor 400 of FIG. 4B after a lead 760 has been inserted in the lead anchor. As previously described with reference to FIG. 6, the lead 760 may be passed through the tubular lead anchor 400 in a variety of configurations. FIG. 7 shows a lead being passed using a single hairpin. As seen in FIG. 7, the addition of the flange 450 helps to stabilize the lead 760 and add rigidity and strength to the tubular lead anchor 400. In some embodiments, the flange 450 further contains suture elements 451 for suturing the anchor to patient tissue. Likewise, FIG. 8 is a schematic view of the tubular lead anchor 500 of FIG. 5 after a lead 860 has been inserted in the lead anchor 500. As previously noted, the tubular lead anchor 500 contains three tubular members providing additional options in securing the lead 860. In some embodiments, as shown in FIG. 8, the lead 860 is passed through the three tubular members to create a double hairpin configuration. A double hairpin configuration may be formed when the lead is disposed through the first opening of the first tubular member, the lead lumen of the first tubular member, and the second opening of the first tubular member, then disposed through the second opening of the second tubular member, the lead lumen of the second tubular member, and the first opening of the second tubular member, then finally disposed through the first opening of the third tubular member, the lead lumen of the third tubular member and the second opening of the third tubular member. As can be appreciated from FIGS. 7 and 8, the tubular lead anchor has the added advantage of being adjustable after a lead has been secured. For example, the tubular lead anchor could be moved along the length of the lead by partially unthreading the lead from one or more of the tubular members.

Figure 9:
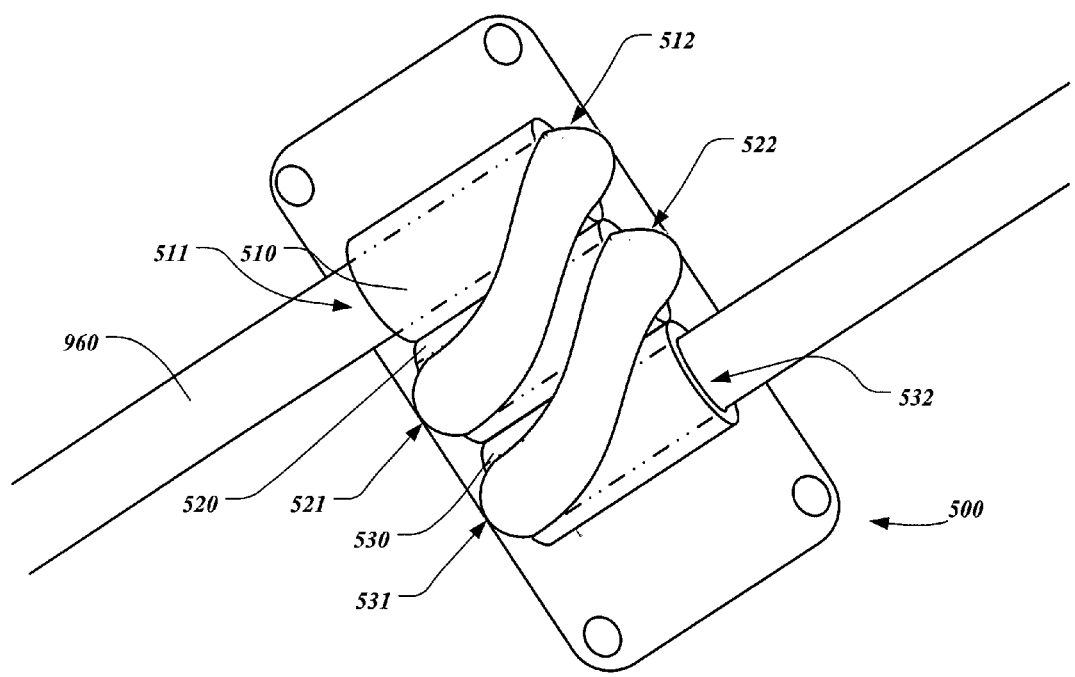
FIG. 9 is a schematic perspective view of the tubular lead anchor of FIG. 5 after a lead has been inserted in the lead anchor using the looping method, according to the invention.

FIG. 9 is a schematic view of the tubular lead anchor 500 of FIG. 5 after a lead 960 has been inserted in the lead anchor 500 using a looping method. As seen in FIG. 9, the lead 960 is introduced through the first tubular member 510. After the lead 960 exits the second opening 512 of the first tubular member 510, it may then be passed through either of the two other tubular members. If the lead is passed across the top of the tubular members and introduced into the first opening 521 of the second tubular member 520, then a loop is formed over the top of the plurality of tubular members. After the lead 960 exits the second opening 522 of the second tubular member 520, a second loop may be formed by introducing the lead 960 into the first opening 531 of the third tubular member 530. In some embodiments, the lead is disposed through the first opening 511 of the first tubular member 510, the lead lumen of the first tubular member, and the second opening 512 of the first tubular member 510, then disposed through the first opening 521 of the second tubular member 520, the lead lumen of the second tubular member, and the second opening 522 of the second tubular member 520, then finally disposed through the first opening 531 of the third tubular member 530, the lead lumen of the third tubular member and the second opening 532 of the third tubular member 530 to create a double loop configuration. By looping the lead 960 instead of introducing it to the adjoining opening of the next tubular member, it is possible to increase the holding strength and more securely hold the lead 960. It is contemplated that the loop may be formed in various configurations. For instance, a loop may be formed between the first tubular member 510 and the third tubular member 530. Furthermore, each of embodiments of the tubular lead anchor discloses above may utilize the lead insertion configurations discussed herein.

Figure 10:
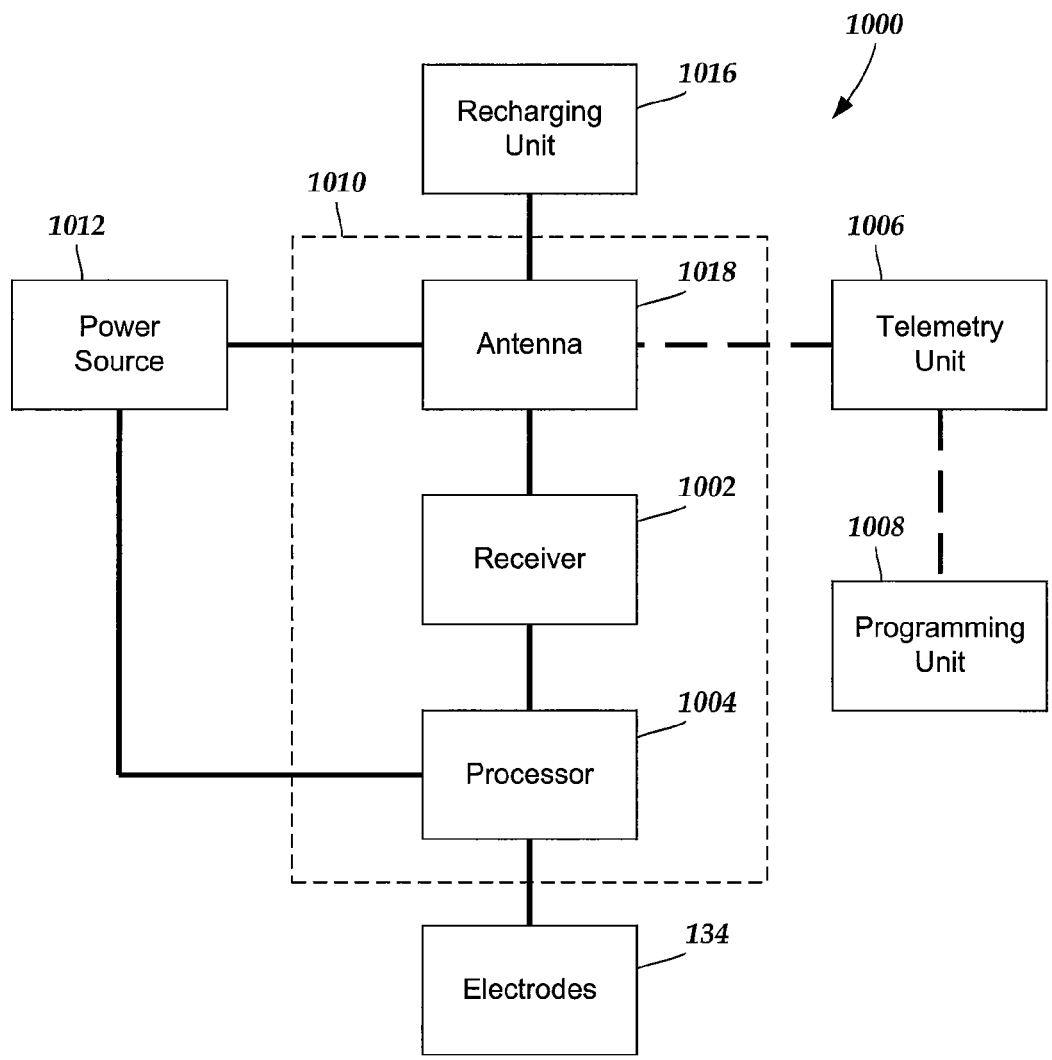
FIG. 10 is a schematic perspective overview of one embodiment of components of an electrical stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In at least one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of implanting an implantable stimulation device, the method comprising:

implanting a portion of a lead having an electrode array near tissue to be stimulated;

securing a distal end of the lead through a lead anchor, the lead anchor comprising a plurality of parallel tubular members, each of the tubular members having a cylindrical exterior surface, wherein the tubular members are lying next to each other side-by-side with the cylindrical exterior surface of each tubular member touching the cylindrical exterior surface of at least one other of the tubular members, each tubular member defining a lead lumen having a first opening and a second opening through which a lead can pass, and at least one suture element configured and arranged for receiving a suture; and securing the lead anchor to the surrounding tissue using sutures.

2. The method of claim 1, further comprising implanting a control module and coupling the electrode array to the control module using a lead.

3. The method of claim 1, wherein the step of securing a distal end of a lead through a lead anchor comprises passing the lead through and looping it around the plurality of parallel tubular members.

4. The method of claim 1, wherein the step of securing a distal end of a lead through a lead anchor comprises passing the lead through at least two adjacent tubular members, forming at least one hairpin turn between the at least two tubular members.

5. The method of claim 1, wherein the step of securing the lead anchor to the surrounding tissue comprises tying a suture to a suture ridge on the tubular member.

6. A lead anchor, comprising:
a plurality of parallel tubular members, each tubular member having a cylindrical exterior surface and defining a lead lumen having a first opening and a second opening through which a lead can pass, the tubular members lying next to each other side-by-side with the cylindrical exterior surface of each tubular member touching the cylindrical exterior surface of at least one other of the tubular members; and
at least one suture element configured and arranged for receiving a suture to suture the lead anchor to patient tissue.

7. The lead anchor of claim 6, further comprising a flange upon which the plurality of tubular members sit and are attached, the flange being formed of a biocompatible material.

8. The lead anchor of claim 7, wherein the flange and the plurality of parallel tubular members are unitary.

9. The lead anchor of claim 7, wherein at least a portion of the plurality of parallel tubular members or the flange is radiopaque.

10. The lead anchor of claim 6, wherein the plurality of parallel tubular members comprises at least three parallel tubular members.

11. The lead anchor of claim 6, wherein the at least one suture element comprises at least one suture opening.

12. The lead anchor of claim 6, wherein, for at least one of the tubular members, the first opening has a larger radius than the second opening.

13. An implantable stimulation device, comprising:
a lead having an electrode array; and
the lead anchor of claim 6, coupleable to the lead.

14. The implantable stimulation device of claim 13, further comprising:
a control module coupleable to the lead.

15. The implantable stimulation device of claim 13, wherein the implantable stimulation device is a spinal cord stimulator.

16. The implantable stimulation device of claim 13, wherein the first opening of each tubular member opens toward a first side of the lead anchor and the second opening of each tubular member opens toward a second side of the lead anchor.

17. The implantable stimulation device of claim 16, wherein the plurality of tubular members comprises a first tubular member and a second tubular member and wherein the lead is disposed through the first opening of the first tubular member, the lead lumen of the first tubular member, and the second opening of the first tubular member, then disposed through the second opening of the second tubular member, the lead lumen of the second tubular member, and the first opening of the second tubular member.

18. The implantable stimulation device of claim 16, wherein the plurality of tubular members comprises a first tubular member and a second tubular member and wherein the lead is disposed through the first opening of the first tubular member, the lead lumen of the first tubular member, and the second opening of the first tubular member, then disposed through the first opening of the second tubular member, the lead lumen of the second tubular member, and the second opening of the second tubular member.

19. The implantable stimulation device of claim 16, wherein the plurality of tubular members comprises a first tubular member, a second tubular member, and a third tubular member and wherein the lead is disposed through the first opening of the first tubular member, the lead lumen of the first tubular member, and the second opening of the first tubular member, then disposed through the first opening of the second tubular member, the lead lumen of the second tubular member, and the second opening of the second tubular member, then finally disposed through the first opening of the third tubular member, the lead lumen of the third tubular member and the second opening of the third tubular member.

20. The implantable stimulation device of claim 16, wherein the plurality of tubular members comprises a first tubular member, a second tubular member, and a third tubular member and wherein the lead is disposed through the first opening of the first tubular member, the lead lumen of the first tubular member, and the second opening of the first tubular member, then disposed through the second opening of the second tubular member, the lead lumen of the second tubular member, and the first opening of the second tubular member, then finally disposed through the first opening of the third tubular member, the lead lumen of the third tubular member and the second opening of the third tubular member.

* * * * *